United States Patent [19]

Kirchnerova et al.

[11] Patent Number: 4,842,698
[45] Date of Patent: Jun. 27, 1989

[54] SOLID STATE ARSENIC PROBE FOR USE IN PYROMETALLURGICAL PROCESSES

[75] Inventors: Jitka Kirchnerova, Montreal; James M. Skeaff, Ottawa; Christopher W. Bale, Montreal, all of Canada

[73] Assignee: Canadian Patents and Development Limited/Société Canadienne des Brevets et d'Exploitation Limitée, Ottawa, Canada

[21] Appl. No.: 52,027

[22] Filed: May 19, 1987

[51] Int. Cl.⁴ .................... G01N 27/58; G01G 28/02
[52] U.S. Cl. .................... 204/1 T; 204/421; 204/427; 423/602
[58] Field of Search ............ 204/421, 424, 1 T, 427; 423/602

[56] References Cited

U.S. PATENT DOCUMENTS

| | | | |
|---|---|---|---|
| 3,843,400 | 10/1974 | Radford et al. | 204/421 X |
| 4,312,733 | 1/1982 | Ninomiya et al. | 204/424 X |
| 4,622,105 | 11/1986 | Liu et al. | 204/1 T |

FOREIGN PATENT DOCUMENTS

| | | | |
|---|---|---|---|
| 1603496 | 11/1981 | United Kingdom | 204/424 |
| 2119933 | 11/1983 | United Kingdom | |
| 2176900 | 1/1987 | United Kingdom | 204/424 |

OTHER PUBLICATIONS

Richard Cote et al., J. Electrochem. Soc., 131, 63, (1984).
Vincent Demuysere et al., Solid State Ionics, 9 & 10, 1285, (1983).
Michel Gauthier et al., Metallurgical Trans., vol. 14B, 117, Mar. 1983.
W. L. Worrell et al., J. Electroanal. Chem., 168, 355–362, (1984).
Yasutoshi Saito et al., Proc. Int. Mtg. on Chemical Sensors (Fukuoka, Japan), p. 326, (1983).
Mitsuru Itoh et al., Trans. Japan Institute of Metals, vol. 25, No. 7, pp. 504–510, (1984).
M. Gauthier et al., J. Electrochem. Soc., vol. 128, No. 2, p. 371, (1981).
J. M. Skeaff et al., Canadian Metallurgical Quarterly, vol. 24, No. 4, pp. 349–362, (1985).
Paul Hagenmuller et al., "Solid Electrolytes", pp. 335–366, Academic Press, (1978).
M. Stanley Whittingham, J. Electrochem. Soc., vol. 118, No. 1, p. 1, (1971).
N. G. Chernorukov et al., "Crystallographic Characteristics of Double Phosphates And Arsenates of Zirconium, $M''ZR_4(PO_4)_6$, $M'ZR_2(ASO_4)_3$, and $M''ZR_4(AsO_4)_6$", Soviet Physics Crystallography, vol. 23, Jan.–Dec. 1978.
K. Tennakone, J. Solid State Chem., 49, 256–257, (1983).
Gene C. Ulmer, "Research Techniques for High Pressure and High Temperature", pp. 43–99, (1971).
J. Kirchnerova et al., Proceedings the Metallurgical Soc. of Cim, 24th Conf. Metallurgists, Aug. 18–21, (1985).
J. Kirchnerova et al., Proceedings, Second Intl. Symposium on Chemical Sensors, Bordeaux, France, Jul. 7–10, (1986).
M. Gauthier et al., "Electrode Processes in Solid State Ionics", Nato Advanced Study Institute, (1975).
M. Gauthier et al., "Solid Electrolytes", C.L. 29, p. 497, Academic Press, (1978).
M. Gauthier et al., J. Electrochem. Soc., 124, 1579, (1977).
M. Gauthier et al., Proc. Int. Mtg. on Chemical Sensors (Fukuoka, Japan), p. 353, (1983).

*Primary Examiner*—G. L. Kaplan

[57] ABSTRACT

A potentiometric electrochemical sensor for detecting gaseous concentrations of arsenic oxides or arsenic-bearing species at elevated temperatures. The sensor is comprised of: an ionically conducting solid state membrane which may be made of silver zirconium arsenate, sodium beta-alumina or silver beta-alumina; a reference electrode which may be silver wire packed in silver powder; and a working electrode which may consist of a platinum mesh electrode or a silver wire exposed to the arsenic oxide-bearing gas. The probe is responsive to arsine [AsH₃] concentrations in the range 5–1000 ppm in oxidizing gases, such as air, which have been raised to the temperature range 600°–900° C. The compound silver zirconium arsentate is also novel.

10 Claims, 1 Drawing Sheet

SOLID STATE ARSENIC PROBE FOR USE IN PYROMETALLURGICAL PROCESSES

This invention is concerned with a simple, robust, potentiometric device, based on a solid electrolyte, for measuring and monitoring the concentration of arsenic oxides in gas phases at elevated temperatures. Typical gas temperatures are of the order of 600° C. to 900° C. This device can then be used both to study the thermal properties of arsenic compounds, and also for monitoring arsenic oxide levels in flue gases.

Arsenic is a highly toxic element which occurs as an impurity in many sulphidic metal ores. The methods of beneficiation used for these ores do not, normally, separate much of the arsenic with the gangue that is removed, for example by froth-flotation. Consequently, when these ores are treated in processes to recover the useful metals in them, the arsenic is still present. In view of the potential toxicity of arsenic compounds, for instance Goth arsine, $AsH_3$, and arsenic oxide-containing gases are lethally toxic at levels below which odour is noticed, a knowledge of both its presence, and, preferably, its amount is desirable. The amount present in an ore after beneficiation can be established by normal analytical procedures.

In many pyrometallurgical processes, for example in the commonly practised roasting of sulphides to provide oxides during the recovery of zinc, copper, iron, nickel, lead, silver or gold (amongst others), much of the arsenic present will also vaporize into the flue gas, as a volatile oxide species, together with the sulphur dioxide also formed. This provides a calcine containing residual amounts of arsenic. It also provides a flue gas which must be treated to remove the vaporized arsenic, which cannot simply be vented to the atmosphere. In order to be able to do this, an effective arsenic sensor is desirable which is both robust enough to withstand the conditions encountered in such flue gases, and which is capable of operating reliably and reproducibly in such an environment.

Devices are known, and used, to monitor sulphur dioxide levels in similar gases, for example coal-fired furnaces and boilers. These sensors are based on observing the behaviour of a solid phase electrolyte which is exposed to the flue gas containing sulphur dioxide [see M. Gauthier et al, "Solid Electyrolytes", Chap. 29, p. 497ff; ed. Hagenmuller & Van Gool, Academic Press, N.Y., 1978]. A number of solid electrolyte systems have been proposed for such devices, including potassium and potassium-silver sulphate solutions; sodium sulphate; two-phase lithium sulphate compositions; and sodium-conducting ceramic materials such as beta-alumina and a complex sodium-zirconia-silica-phosphate known as "NASICON" (the formula generally given for this material is $Na_3Zr_2Si_2PO_{12}$). Additionally, various reference electrodes have been proposed for these sulphur dioxide sensors, including noble metals and certain alloys, circulating gases, and stationary gases. These devices have found a level of commercial acceptance.

These sulphur dioxide sensors utilize the fact that the thermodynamic data both exists, and is known to be reliable, for the sulphur oxides and a number of sulphate systems. For arsenic oxides and the related arsenates the position is very different. The thermodynamic data that exists is both incomplete, and much of it is of doubtful reliability (for example, due to different workers reporting different data for what should be the same species). At least one reason for this seems to be the difficulties attendant upon handling arsenic-containing compounds. As is noted above, arsine is lethal at levels of the order of 1 ppm, at which level detection of its odour is unreliable: this is not the case for hydrogen sulphide This fact markedly complicates the study of metal arsenides Furthermore, whilst the nature of the sulphur oxides to be expected in the off-gas from a sulphide-roasting step is well known, this is certainly not the case for arsenic. For example, it has been shown that, at the order of temperature which can be expected in a flue gas, the vapour in equilibrium with solid arsenic pentoxide appears to contain at least five arsenic oxide species each having different arsenic:oxygen ratios.

For gas sensing devices of this type, the material to be used for the solid electrolyte membrane needs to have certain desirable properties. It should have sufficient mechanical and chemical stability to withstand the rigorous conditions encountered in a flue gas, especially as regards to the ability to withstand thermal cycling in a range of from around 800° C. down to about 20° C. during periods of furnace shut-down and start-up. It should be responsive both to the presence of arsenic oxides, and to changes in the amounts present. It should exhibit both stability and reproducibility in terms of the electrical signals derivable from it. These parameters point toward a ceramic-like material as being most likely to provide a workable balance of these properties.

We have now discovered a group of materials which meet these onerous requirements, thus making it possible to fabricate a solid-electrolyte sensor for arsenic oxides.

Thus in its broadest aspect, this invention provides an arsenic oxide sensor adapted to operate at a temperature in the range of from about 600° C. to about 900° C. comprising, in combination, a reference electrode, a working electrode, and in electrical connection therewith a solid electrolyte chosen from sodium zirconium arsenate $(NaZr_2(AsO_4)_3)$, silver zirconium arsenate $(AgZr_2(AsO_4)_3)$, sodium beta-alumina, and silver beta-alumina.

Preferably, the cell will also include a thermocouple, either by utilizing at least one of the electrode leads, or by incorporating a separate thermocouple. A convenient thermocouple is the well-known Pt/Pt+10% Rh sensor.

The working electrode should be a noble metal compatible with the solid electrolyte: both silver and platinum are suitable metals.

The reference electrode offers a wider range of choice. It can be a stationary gas, or a moving gas, or a noble metal. For a gas electrode, pure air provides an adequate gas containing a constant amount of oxygen. For a noble metal, both silver and platinum have been found suitable.

The invention will now be discussed in detail by way of reference to the attached drawings in which.

Figure 1:
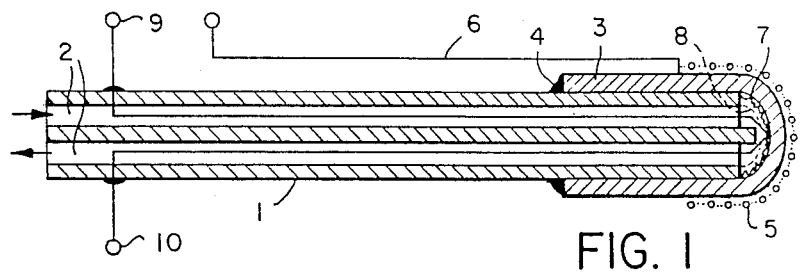
FIG. 1 represents a sensor with an external reference electrode.
Figure 2:
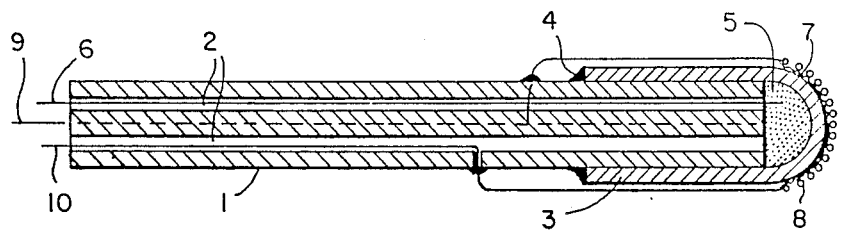
FIG. 2 represents a sensor with an internal reference electrode.
Figure 3:
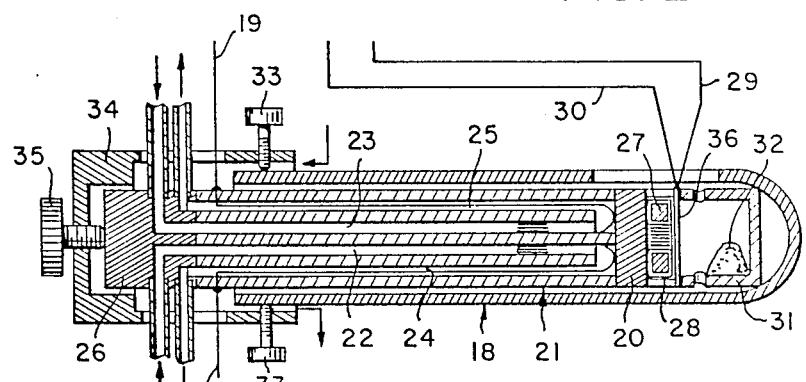
FIG. 3 represents a sensor suitable for evaluating electrolyte materials.

The configurations of FIGS. 1 and 2 are more suitable for use, with suitable shielding and gas conduits, in a furnace environment than that of FIG. 3, as they do not contain small-bore passages through which the gases containing arsenic oxides have to pass.

Referring first to FIGS. 1 and 2 both of these are based on an alumina tube 1 having therein four bores (only two are shown for clarity), 2. These four bores are used as needed for the electrical leads, thermocouple leads, and as flow tubes for air if used as the reference electrode. In each of these probes the solid electrolyte is a thin thimble-shaped element 3, cemented to the end of the alumina tube over a suitable length, as at 4. Thereafter the constructions of these two probes differs, as the reference electrodes are differently placed.

In the arrangement of FIG. 1, the electrode thimble 3 is silver beta-alumina. The reference silver electrode 5 is attached to silver wire 6 which is closely wound onto the outside of the probe. The inner surface of the thimble 3 is platinized, 7, and a working platinum mesh electrode, 8, attached thereto. This electrode is then connected to the Pt/Pt-Rh thermocouple leads 9, 10 to complete the electrical circuit and to provide temperature measurement.

In the arrangement of FIG. 2, the same parts, essentially, are used, but arranged differently. The platinum working electrode 8 is now on the outside of the thimble 3 in contact with the platinized surface 7. The thermocouple leads 9, 10 for the Pt/Pt-Rh thermocouple, again complete the electrical circuit. The silver reference electrode 5 comprises silver metal powder packed into the end of the tube.

These probes require the ability to form the thimble shape 3 for the solid electrolyte. For testing purposes, for example, it is desirable to be able to avoid this somewhat complicated step. The arrangement of FIG. 3 can then be used. This probe also permits the use of a stationary gas electrode, as will be seen hereafter.

In this probe, a disc of electrolyte, 20, is the central portion. To one side of this is provided a multiple bore tube 21 through which the test gas flows: in the figure there are four bores, two being used for gas in-flow (22,23) and two being used for gas exhaust (24,25). The alumina tube is sealed to a suitable manifold block 26. Two of these tubes also contain metal electrodes, 19, which bear against the side of the pellet 20 exposed to the test gas.

On the other side of the pellet 20 two arrangements are possible. In one configuration, a simple metal disc is pressed up against the pellet as working electrode, the other metal electrodes then functioning as the reference electrodes. Alternatively, the alumina crucible 31 can be provided with a reaction mixture 32 which will decompose (for example on heating to the test temperature) to provide a stationary gas reference electrode. Contact to the pellet 20 is then made through a metal electrode wire 28, for example platinum, wound onto the alumina ring 27 which is pressed against the pellet 20. Electrical contact to this ring is then made through a metal gauze 36, and the thermocouple leads 29 and 30.

The probe as a whole is retained within an outer alumina tube 18 retained by screws 33 in a cap 34, also provided with a screw 35 which, by compressing the various parts against the far end of the tube 18, maintains a gas-tight seal between the various parts of the probe. For a probe for extended use, a suitable ceramic adhesive could be used to hold the parts together.

Using one or other of these designs, a variety of combinations of working electrode, solid electrolyte, and reference electrode have been evaluated under various differing conditions. For these tests, a synthetic gas system was used containing arsenic oxides. Two sources were used.

In some experiments, the arsenic oxide containing gas was obtained by the quantitative oxidation of arsine $AsH_3$, with oxygen. A catalyst was also employed to ensure complete reaction.

In other experiments, the arsenic oxide containing gas was obtained by passing a carrier gas over a quantity of arsenolite maintained at a suitable temperature, for example, 150° C. in a stainless steel container; a thermostated oil heating system was used.

For both of these methods, the carrier gas used was nitrogen, oxygen and nitrogen, or air; in each case commercial high purity extra-dry gases were used without any further treatment. Steps were also taken to ensure that the apparatus was gas tight, and also to remove any arsenic oxide species from the vented gases, by scrubbing with a sodium hydroxide solution.

The solid electrolytes used were either synthesized, or, in the case of the sodium beta-aluminas, obtained as a commercial product. The silver beta-alumina was obtained by ion-exchange, achieved by soaking sodium beta-alumina in silver nitrate. The other electrolytes were synthesized by grinding the required amounts of each component (in a mortar), blending, and heating. The weight loss on heating was found to be an adequate indicator of reaction progress, and heating was terminated when the theoretical weight loss had occurred. These powders were then pressed (10T cm$^{-2}$ for 2 min.) to provide a pellet, which was then sintered. The details of these steps are shown in the following Table.

TABLE

CONDITIONS FOR THE SYNTHESIS OF SOLID ELECTROLYTES

| ELECTROLYTE | INITIAL COMPOUNDS | INITIAL WEIGHT g | YIELD g | HEATING °C. | hr | SINTERING °C. | hr |
|---|---|---|---|---|---|---|---|
| $NaZr_2(AsO_4)_3$ | $Na_2CO_3$ | 0.53 | | 190 | 18 | 500 | 6 |
| | $Zr(SO_4)_2.4H_2O$ | 7.108 | 6.08 | 560 | 20 | then steps of | |
| | $As_2O_5.H_2O^a$ | 4.312 | 98.9% | and finally | | 100 | 1 |
| | | | | 890 | | of 1200 | 16 |
| $AgZr_2(AsO_4)_3$ | $AgNO_3$ | 1.698 | | 180 | 18 | | |
| | $Zr(SO_4)_2.4H_2O$ | 7.108 | 6.84 | 560 | 12 | then steps of | |
| | $As_2O_5.H_2O^a$ | 4.312 | 99.2% | and finally | | 100 | 2 |
| | | | | 750 | 18 | of 940 | 12 |

$^a$19.9% water by chemical analysis
$^b$35.1% $ZrO_2$ by drying and calcination In each case, the sensor was also provided with a Pt/Pt-10% Rh thermocouple. Corrections were also made, where necessary, for any thermoelectric effects from any Ag—Pt junctions.

The selected solid electrolytes were evaluated with respect to their response to different temperatures, and to various arsenic oxide species and oxygen concentrations in gases in contact with them.

1. Sodium Calcium Arsenate: NaCaAsO$_4$

This material was evaluated using the cells (a) Pt, air, P$_{As_4O_6}$/NaCaAsO$_4$/P$_{AsH_3}$, P$_{O_2}$Pt and (b) Pt, air, Ag, Ag$_3$AsO$_4$/NaCaAsO$_4$/P$_{AsH_3}$, P$_{O_2}$, Pt in the apparatus of FIG. 3. In each case, the cells responded both to change in temperature and to change in the quantity of arsenic oxide species being presented to the cell. At a constant temperature, a plot of EMF vs. the log of the arsenic concentration is approximately linear. The EMF appears to decrease with increasing temperatures.

Typical EMF readings for these cells are as follows, using air containing 1–3 ppm of As$_4$O$_6$ as the reference gas and air containing 100 ppm arsine as the test gas:

at 802° C.: 190 millivolts
at 744° C.: 295 millivolts
at 776° C.: 310 millivolts 2. Silver beta-Alumina This solid electrolyte was evaluated using the designs of both FIG. 1 and FIG. 2. In each case the cell is the same, and is typically Ag/Ag$^+$-beta-alumina/P$_{AsH_3}$, P$_{O_2}$, Pt. In each case, the cells were found to respond almost instantaneously to the presence of arsenic oxide species, but took a considerable time initially to reach a steady EMF. Thereafter, as was observed with other solid electrolytes, after what may be described as an initial conditioning, response became far more rapid, being of the order of 5 to 30 minutes, but still longer than the response times observed for both silver zirconium arsenate and sodium calcium arsenate. It was however observed that the FIG. 2 arrangement is somewhat less sensitive to concentration changes than that of FIG. 1. Both arrangements showed good reproducibility of results both over extended time periods, and after thermal cycling (of the FIG. 1 arrangement) in the range 680° C. to 910° C.

A typical EMF reading for this cell is a value of 305 millivolts, using hot air containing 1000 ppm arsine as the test gas, and silver beta-alumina as the reference.

3. Sodium beta-Alumina

This was evaluated in the same way as silver beta-alumina and showed much the same properties, both as regards an initial response being slow, and response to changes thereafter being much more rapid. Reproducibility over periods of several days was also found to be acceptable. This material also showed two further advantages. It appears to be far less sensitive to gas flow rate than the silver beta-alumina, and also does not seem to have an upper sensitivity limit, at least up to 3960 ppm arsine in the feed test gas, again unlike the silver beta-alumina.

A typical EMF reading for this cell is a value of 675 millivolts using air as the reference, and hot air containing 301 ppm arsine as the test gas.

It is noted above that these probes find use in furnace applications. They can also be used to test cooler air, for example a sample of air at ambient temperature, suspected to contain, for example, arsine. All that is necessary is to provide a means to heat the air, for example a small furnace, to a desired temperature at which the probe will function.

What we claim as our invention is:

1. The compound silver zirconium arsenate of the formula AgZr$_2$(AsO$_4$)$_3$.

2. An arsenic oxide species sensor adapted to operate at a temperature in the range of from about 600° C. to about 900° C. comprising in combination:
   a reference electrode;
   a working electrode; and
   in electrical connection therewith, a solid electrolyte chosen from sodium zirconium arsenate [NaZr$_2$(AsO$_4$)$_3$] and silver zirconium arsenate [AgZr$_2$(AsO$_4$)$_3$].

3. A sensor according to claim 2 wherein both the electrodes are a noble metal compatible with the solid electrolyte.

4. A sensor according to claim 3 wherein the electrodes are silver or platinum.

5. A sensor according to claim 4 wherein the working electrode is platinum.

6. A sensor according to claim 2 wherein the reference electrode is a gas.

7. A sensor according to claim 5 wherein the gas is air.

8. A method of detecting arsenic oxides in a gas in the temperature range of from about 600° C. to about 900° C. which comprises exposing the solid electrolyte in a cell comprising a working electrode, a solid electrolyte, and a reference electrode to the gas, and observing the EMF generated by the cell, wherein the solid electrolyte is chosen from sodium zirconium arsenate [NaZr$_2$(AsO$_4$)$_3$] and silver zirconium arsenate [AgZr$_2$(AsO$_4$)$_3$].

9. A method according to claim 8 wherein the gas contains arsine, AsH$_3$, which is oxidized under the conditions of detection.

10. A method according to claim 8 wherein a sample of gas is heated to from about 600° C. to about 800° C. for detection purposes.

* * * * *